(12) United States Patent
Jordan et al.

(10) Patent No.: US 9,233,064 B2
(45) Date of Patent: *Jan. 12, 2016

(54) HAIR FIXATIVES

(75) Inventors: Susan Jordan, Doylestown, PA (US); Miao Wang, Schwenksville, PA (US); Andrea Keenan, Plymouth Meeting, PA (US)

(73) Assignees: Rohm and Haas Company, Philadelphia, PA (US); Union Carbide Chemicals & Plastics Technology LLC, Midland, MI (US)

( * ) Notice: Subject to any disclaimer, the term of this patent is extended or adjusted under 35 U.S.C. 154(b) by 179 days.

This patent is subject to a terminal disclaimer.

(21) Appl. No.: 13/822,781

(22) PCT Filed: Oct. 12, 2011

(86) PCT No.: PCT/US2011/055953
§ 371 (c)(1),
(2), (4) Date: Mar. 13, 2013

(87) PCT Pub. No.: WO2012/054278
PCT Pub. Date: Apr. 26, 2012

(65) Prior Publication Data
US 2013/0195788 A1 Aug. 1, 2013

Related U.S. Application Data

(60) Provisional application No. 61/394,947, filed on Oct. 20, 2010.

(51) Int. Cl.
*A61K 8/81* (2006.01)
*A61Q 5/06* (2006.01)
*A61K 8/04* (2006.01)

(52) U.S. Cl.
CPC ................ *A61K 8/8152* (2013.01); *A61K 8/04* (2013.01); *A61K 8/8111* (2013.01); *A61Q 5/06* (2013.01)

(58) Field of Classification Search
CPC ..... A61Q 5/06; A61K 8/8152; A61K 8/8111; A61K 8/04
See application file for complete search history.

(56) References Cited

U.S. PATENT DOCUMENTS

| | | | |
|---|---|---|---|
| 4,599,392 A | 7/1986 | McKinney et al. | |
| 4,701,432 A | 10/1987 | Welborn, Jr. | |
| 4,988,781 A | 1/1991 | McKinney et al. | |
| 5,272,236 A | 12/1993 | Lai et al. | |
| 5,322,728 A | 6/1994 | Davey et al. | |
| 5,938,437 A | 8/1999 | DeVincenzo | |
| 6,525,157 B2 | 2/2003 | Cozewith et al. | |
| 6,960,635 B2 | 11/2005 | Stevens et al. | |
| 2004/0247552 A1* | 12/2004 | Blin et al. | 424/70.13 |
| 2005/0169865 A1* | 8/2005 | Parris | 424/70.11 |
| 2006/0013840 A1* | 1/2006 | Lamberty et al. | 424/401 |
| 2006/0088495 A1* | 4/2006 | Harichian et al. | 424/70.28 |
| 2007/0269392 A1* | 11/2007 | Sunkara | 424/59 |
| 2008/0031840 A1* | 2/2008 | Wolff et al. | 424/70.9 |
| 2009/0010855 A1* | 1/2009 | Lepilleur et al. | 424/47 |
| 2010/0119467 A1* | 5/2010 | Dumousseaux et al. | 424/70.7 |
| 2010/0310671 A1 | 12/2010 | Malotky et al. | |
| 2011/0064685 A1 | 3/2011 | Jordan | |
| 2011/0064686 A1 | 3/2011 | Zhang et al. | |
| 2011/0064688 A1 | 3/2011 | Jordan et al. | |
| 2011/0236334 A1* | 9/2011 | Jordan et al. | 424/70.6 |

FOREIGN PATENT DOCUMENTS

| | | | |
|---|---|---|---|
| EP | 2168563 A2 * | 3/2010 | |
| WO | 2006/028931 A2 | 3/2006 | |
| WO | WO 2009064739 A1 * | 5/2009 | |

OTHER PUBLICATIONS

Amerchol, Kytamer PC, DOW (2004) downloaded from http://msds-search.dow.com/PublishedLiteratureDOWCOM/dh_0039/0901b80380039e2a.pdf?filepath=amerchol/pdfs/noreg/324-00182.pdf&fromPage=GetDoc.*
McKay, Humidity, Humectants and Hair, Aug. 1, 2007, accessed at http://www.naturallycurly.com/curlreading/curl-products/curlchemist-humidity-humectants-and-hair, on Jul. 1, 2015.*
Katagiri, et al., Cover material for foodstuf containers, comprises resing layer containing polyethylene, polypropylene, ionomer, ethylene acrylic acid copolymer and/or ethylene methacrylic acid copolyer, vol. 2003, No. 10, 2002. Abstract only.
Wakabayashi, et al., Micromechanical interpretation of the modulus of ethylene-(meth)acrylic acid copolymers, Polymer, vol. 46, No. 20, pp. 8838-8848, 2005.

* cited by examiner

*Primary Examiner* — Bethany Barham
*Assistant Examiner* — Lisbeth C Robinson
(74) *Attorney, Agent, or Firm* — Edward L. Brant

(57) ABSTRACT

Described are hair fixative compositions comprising an aqueous dispersion comprising an ethylene acrylic acid co-polymer, and optionally a metallocene catalyzed polyolefin.

12 Claims, No Drawings

HAIR FIXATIVES

CROSS REFERENCE TO RELATED APPLICATIONS

This application is a 35 USC §371 national phase filing of PCT/US2011/055953 filed Oct. 12, 2011, which claims the benefit of U.S. Application No. 61/394,947, filed Oct. 20, 2010.

FIELD

The present application relates to personal care compositions, more specifically, hair fixatives.

BACKGROUND

Hair fixatives (sprays, mousses, pomades, gels, and the like) are designed to hold hair in a particular arrangement styled by the user. To achieve long lasting hold, the treated hair must be resilient to stress and resistant to humidity. While this can be accomplished by a number of cosmetically acceptable materials in theory, at the same time the hair fixative must also be able to be removed by shampoo. Moreover, aesthetic considerations of the hair fixative upon drying are of paramount importance to users, particularly shine, combability, and feel. Users value a soft feel, but heretofore have assumed that they have to sacrifice feel in order to obtain superior holding properties, or vice versa.

Accordingly, what is needed is new hair fixative compositions that hold well, are readily removable with shampoo, and demonstrate improved aesthetics.

SUMMARY

In one embodiment, the present invention provides hair fixative compositions, comprising an aqueous dispersion comprising an ethylene acrylic acid copolymer, and optionally, a metallocene catalyzed polyolefin.

DETAILED DESCRIPTION

In one embodiment, the present invention provides hair fixative compositions, comprising an aqueous dispersion comprising an ethylene acrylic acid copolymer, and optionally a metallocene catalyzed polyolefin.

In the present invention, "hair fixative" is intended to refer to personal care compositions for styling hair, such as sprays, mousses, pomades, and gels. "Personal care" relates to compositions to be topically applied to a person (i.e., not ingested). Preferably, the personal care composition is cosmetically acceptable. "Cosmetically acceptable" refers to ingredients typically used in personal care compositions, and is intended to underscore that materials that are toxic when present in the amounts typically found in personal care compositions are not contemplated as part of the present invention.

Copolymerizing ethylene with acrylic acid yields ethylene-acrylic acid (EAA) copolymers. A preferred ethylene acrylic acid copolymer comprises greater than about 15 wt % acrylic acid, preferably greater than about 17 wt % acrylic acid, more preferably about 20 wt % acrylic acid. It should be understood that ranges recited in this disclosure include all subcombinations of ranges.

A preferred EAA copolymer is PRIMACOR 5990 copolymer (20 wt % acrylic acid), which has a melt index of 1300 g/10 minute (ASTM Method D-1238 at 190° C.) and a Brookfield viscosity of 13,000 cps at 350° F., and is available from The Dow Chemical Company. Another preferred EAA copolymer is PRIMACOR 5980i copolymer (20.5 wt % acrylic acid), which has a melt index of 300 g/10 minute (ASTM Method D-1238 at 190° C.), available from The Dow Chemical Company. EAA copolymers are also available under the tradename NUCREL 2806, available from E.I. du Pont de Nemours and Company, Inc. Ethylene-acrylic acid and ethylene-methacrylic acid copolymers, are described in U.S. Pat. Nos. 4,599,392, 4,988,781, and 5,938,437, each of which is incorporated herein by reference in its entirety.

Metallocene catalyzed polyolefins are polyolefins produced with a metallocene catalyst as described in U.S. Pat. Nos. 4,701,432, 5,322,728, and 5,272,236, each of which is incorporated herein by reference in its entirety. As a specific embodiment of the present invention, the metallocene catalyzed polyolefins are polyethylenes produced with a metallocene catalyst. Such metallocene catalyzed polyethylenes are available e.g. from The Dow Chemical Company under the trademark AFFINITY or ENGAGE (ethylene/octene copolymers) and from Exxon Chemical Company under the trademark EXACT (ethylene/butene copolymers, ethylene/hexene copolymers, or ethylene/butene/hexene terpolymers). In one embodiment, the metallocene catalyzed polyolefin is at least one of ethylene/octene copolymers, ethylene/butene copolymers, ethylene/hexene copolymers, ethylene/propylene or ethylene/butene/hexene terpolymers, preferably an ethylene octene copolymer.

In another embodiment, the metallocene catalyzed polyolefin is a propylene/alpha-olefin copolymer, which is further described in details in the U.S. Pat. Nos. 6,960,635 and 6,525,157, each of which is incorporated herein by reference in its entirety. Such propylene/alpha-olefin copolymers are commercially available from The Dow Chemical Company, under the tradename VERSIFY™, or from ExxonMobil Chemical Company, under the tradename VISTAMAXX™. In one embodiment, the metallocene catalyzed polyolefin is a ethylene/alpha-olefin copolymer, which is commercially available from The Dow Chemical Company, under the tradename INFUSE™.

In one embodiment, the ethylene acrylic acid copolymer and metallocene catalyzed polyolefin are melt-kneaded in an extruder along with water and a neutralizing agent, such as ammonia, potassium hydroxide, sodium hydroxide, or a combination of the two, to form an aqueous dispersion.

Mechanical dispersion, such as a Parr reactor, is used to create the aqueous dispersion.

In one embodiment, the metallocene catalyzed polyolefin comprises at least one of ethylene/octene copolymers, ethylene/butene copolymers, ethylene/hexene copolymers, or ethylene/butene/hexene terpolymers, preferably a ethylene octene copolymer.

The ethylene acrylic acid copolymer is present in a range from about 2 wt % to about 35 wt % by weight of the aqueous dispersion, preferably in a range from about 4 wt % to about 20 wt %.

In one embodiment, the metallocene catalyzed polyolefin is present in a range from about 10 wt % to about 50 wt % by weight of the aqueous dispersion, preferably in a range from about 15 wt % to about 40 wt %.

Typically, the ethylene acrylic acid copolymer and metallocene catalyzed polyolefin is in a polymer ratio of about 40:60 to about 15:85.

The solids content of the aqueous dispersion is in a range from about 10% by weight to about 50% by weight, preferably about 40% by weight.

In turn, the aqueous dispersion is present in a range from about 0.5 wt % to about 10 wt % of solids, preferably about 1 wt % to about 5 wt %, by weight of the personal care composition.

In one embodiment, the hair fixative composition optionally comprises a hair fixative resin. Suitable hair fixative resins include those acrylates sold by The Dow Chemical Company under the tradename ACUDYNE, and those chitosan polymers sold by The Dow Chemical Company under the tradename KYTAMER.

In one embodiment, the hair fixative composition optionally comprises a conditioning agent. Suitable conditioning agents include those quaternary ammonium salts of hydroxyethyl cellulose (Polyquaternium 67) sold by The Dow Chemical Company under the tradename SOFTCAT, those polymeric, quaternary ammonium salts of hydroxyethyl cellulose polymers (Polyquaternium 10) sold by The Dow Chemical Company under the tradename UCARE, and preferably dihydroxypropyl trialkyl ammonium chloride sold by The Dow Chemical Company under the tradename PD QUAT, and described generally in U.S. Pat. No. 7,541,496, the entirety of which is incorporated herein by reference.

In one embodiment, the conditioning agent is a quaternary trialkylammonium halide compound following the formula:

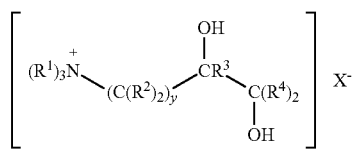

wherein the $R^1$ groups are each individually selected from the group consisting of alkyl groups having from 1 to 12 carbon atoms; wherein the $R^2$, $R^3$, and $R^4$ groups are each individually selected from the group consisting of hydrogen, hydroxide, alkyl groups having from 1 to 12 carbon atoms, and hydroxy alkyl groups having from 1 to 12 carbon atoms; wherein y ranges from 0 to 12; wherein $X^-$ is selected from the group consisting of fluoride, chloride, bromide, and iodide. Preferably, the $R^1$ groups are each individually alkyl groups having from 1 to 12, preferably 1 to 6, carbon atoms; the $R^2$, $R^3$, and $R^4$ groups are each hydrogen or alkyl groups having from 1 to 6, preferably 1, carbon; y is 0 or 1; and $X^-$ is chloride.

The amount of optional ingredients effective for achieving the desired property provided by such ingredients can be readily determined by one skilled in the art. In use, the hair fixative compositions are applied to hair in a conventional manner.

EXAMPLES

The following examples are for illustrative purposes only and are not intended to limit the scope of the present invention. All percentages are by weight unless otherwise specified.

Example 1

Personal care compositions of the present invention include aqueous dispersions comprising an ethylene acrylic acid copolymer. Examples of such aqueous dispersions include the following:

Batch 1

A 41.7% solids aqueous dispersion of ethylene acrylic acid and metallocene catalyzed polyolefin, commercially available from The Dow Chemical Company under the tradename HYPOD 8510, produced using Dow's BLUEWAVE technology.

Batch 2

PRIMACOR 5980i 20% ethylene acrylic acid resin (60 g), potassium hydroxide (25 g of 30 wt. %), and water (21 g) are placed in a 300 mL Parr reactor vessel fitted with a Cowles blade. The material is heated to 120° C. while mixing slowly. Once the set temperature is reached, the mixer is run on high (1800 rpm) for 25 minutes. While still mixing on high, the sample is diluted with water fed into the reactor with an HPLC pump at a rate of 40 mL/min to the desired concentration of 25.7% solids by weight based on the amount of ethylene acrylic acid resin. Heat is removed and stirring continues until the temperature cools to at least 45° C. The Parr is then opened and the dispersion is collected.

Example 2

Exemplary hair fixatives of the present invention contain the components recited in TABLE 1 on a weight/weight basis (wt. %).

TABLE 1

|  | Batch A | Batch B | Batch C | Batch D |
|---|---|---|---|---|
| Batch 1 Ethylene/octane copolymer and ethylene/sodium acrylate copolymer (41.7%) | 4.5 | 4.5 | — | — |
| Batch 2 ethylene/sodium acrylate copolymer (25.7%) | — | — | 6.9 | 6.9 |
| ACULYN 88 Acrylates/Steareth-20 Methacrylate Crosspolymer | 2.5 | 4.0 | 2.5 | 4.0 |
| NEOLONE PE Phenoxyethanol/methylisothiazlinone | 1 | 1 | 1 | 1 |
| AMP - ULTRA PC Amino methylpropanol | 0.25 | 0.5 | 0.25 | 0.5 |
| Water | 91.75 | 90.0 | 89.35 | 87.6 |

Components other than AMP PC Ultra are combined in a beaker with overhead stiffing at about 350 rpm. AMP PC Ultra is gradually added dropwise until clear hair gel is formed.

Example 3 (Comparative)

Comparative hair fixatives contain the components recited in TABLE 2 on a weight/weight basis (wt. %).

TABLE 2

|  | Comparative Batch Y | Comparative Batch Z |
|---|---|---|
| ACULYN 88 Acrylates/Steareth-20 Methacrylate Crosspolymer | 2.5 | 4.0 |
| NEOLONE PE Phenoxyethanol/methylisothiazlinone | 1 | 1 |
| AMP - ULTRA PC Amino methylpropanol | 0.25 | 0.5 |
| Water | 96.26 | 94.5 |

Comparative Batches Y and Z are prepared substantially according to the protocol of Example 2. The following commercially available hair fixatives were also procured:
Comparative Batch V: LA LOOKS—8 MEGA HOLD based on PVP (polyvinyl pyrrolidone), Polyquaternium-7, commercially available from Henkel Corporation Comparative Batch W: TRESEMME SMOOTHING CRÈME—FRIZZ CONTROL—based on PVP commercially available from Alberto-Culver Company Comparative Batch X: VITAL CARE EPDXY HAIR GLUE (EXTREME HOLD FOR HI-DEF STYLING)—based on PVP, Methacryloyl Ethyl Betaine/Acrylates Copolymer commercially available from Valley Medical Pharmacy (Brawley Calif.) or www.drugsdepot.com.

Example 4

Compositions substantially according to the protocols of Examples 2 and 3 were prepared. Pre-washed and dried tresses of Brazilian Curly hair and European virgin brown hair (both available from International Hair Importers and Products Inc.) were tested in duplicate.

Hold

To determine hold, mild shampoo was applied to the hair tresses and dried on a curler over night. The curled tresses were uniformly sprayed twice in the front and twice on the back from a distance of about 20.3 centimeters (cm) with the hair spray formulation listed in TABLE 3. The spray device dispensed 190 μL (microliters) of formulation with each compression. The spray device product was "Euromist Classic" and was manufactured by SequistPerfect, Cary, Ill. The curled, treated tresses were dried for 1 hour in a controlled environment at 22.5 ° C. and 55% relative humidity. The curler was removed carefully without uncurling the tress. The curled tress was placed in the miniature tensile tester, model MTT160 instrument (Dia-Stron Limited, Unit 9 Focus 303 Business Centre, Andover, Hampshire SP10 5NY UK, or 390 Reed Road, Broomall, Pa. 19008, USA) and the work to compress the curl to 50% of its initial diameter was measured. The compression was repeated 5 times for each tress. Measurements were made at about 22.5 ° C. and 55% relative humidity. The results of curl compression tests for tresses treated with the listed compositions are recited in TABLE 3:

TABLE 3

|  | European Tresses | | Brazilian Tresses | |
| --- | --- | --- | --- | --- |
|  | First Compression | Fifth Compression | First Compression | Fifth Compression |
| Batch A | 1149 | 682 | 907 | 798 |
| Batch B | 1297 | 754 | 574 | 411 |
| Batch C | 629 | 341 | 720 | 448 |
| Batch D | 1247 | 593 | 1270 | 790 |
| Comparative Batch V | 968 | 652 | 1045 | 771 |
| Comparative Batch W | 116 | 107 | 312 | 255 |
| Comparative Batch X | 899 | 782 | 1233 | 273 |
| Comparative Batch Y | 529 | 363 | 522 | 450 |
| Comparative Batch Z | 905 | 659 | 272 | 133 |

The higher the compression the number is, the stiffer the hair. The results show the inventive compositions produce hair curls as stiff as commercial products designed for high hold. In addition, inventive compositions hold the curl well after five compressions.

High Humidity Curl Retention

To determine high humidity curl retention, humidity resistance of hair styling polymers at 35° C. and 95% relative humidity over a period of time. The initial length was measured after the curler was removed, and the length of the curl drop was monitored over time after exposure to humidity. A ratio of the change of length compared to the fully extended length is calculated. A lower change in percentage curl retention versus time is an indication of longer lasting hold performance of a hair styling product. Values are the average of two hair tresses placed at 35° C., 95% humidity for the times listed in the table. Initial curl retention for each sample is normalized to 100 for comparison purposes. The results of high humidity curl retention tests for tresses treated with the listed compositions are recited in TABLE 4:

TABLE 4

|  | European Tresses | | | | Brazilian Tresses | | | |
| --- | --- | --- | --- | --- | --- | --- | --- | --- |
|  | init. | 2 | 4 | 8 | init. | 2 | 4 | 8 |
| Batch A | 100 | 100 | 95 | 95 | 100 | 95 | 90 | 80 |
| Batch C | 100 | 90 | 90 | 90 | 100 | 80 | 60 | 50 |
| Comparative Batch V | 100 | 50 | 20 | 20 | 100 | 65 | 30 | 10 |
| Comparative Batch W | 100 | 50 | 20 | 20 | 100 | 70 | 50 | 20 |
| Comparative Batch X | 100 | 40 | 20 | 10 | 100 | 50 | 20 | 20 |
| Comparative Batch Y | 100 | 90 | 85 | 80 | 100 | 85 | 70 | 60 |

Results show that the inventive compositions outperform the commercial fixatives in retention of curl over time.

Aesthetics

The above shows that the inventive compositions demonstrate excellent hold properties, but traditionally, a trade off must be made between hold and aesthetics. Brazilian hair tresses treated as above were hung for a dry sensory evaluation study. Three expert panelists trained to evaluate the performance of cosmetic products on hair were asked to evaluate combability, flaking, and feel in the dry stage. Each panelist evaluated three tresses of each type. The panelists were asked to rate each tress from 1-10 (10 being best). Results are reported in TABLE 5.

TABLE 5

|  | Dry Comb | Flaking | Dry Feel |
| --- | --- | --- | --- |
| Batch A | 7 | 8 | 6.5 |
| Batch B | 8 | 9 | 8 |
| Batch C | 8 | 9 | 9 |
| Batch D | 9 | 9.5 | 9 |
| Comparative Batch V | 6 | 6 | 6 |
| Comparative Batch X | 4.5 | 8 | 6 |

The comparative batches with the best stiffness generally did not have aesthetics that were as good as the inventive compositions.

Example 5

Compositions substantially according to the protocols of Examples 2 and 3 were prepared. Pre-washed and dried tresses of Curly/Kinky hair (available from International Hair Importers and Products Inc.) were tested. Frizz is a subjective evaluation of a hair tress. After exposure to humidity, trained panelists observe extended sides and excessive curliness compared to original tresses. Results are reported in TABLE 6.

TABLE 6

|  | Observations |
| --- | --- |
| Batch A | Slightly stiff, no frizz |
| Batch B | Slightly stiff, no frizz |

TABLE 6-continued

| | Observations |
|---|---|
| Comparative Batch V | Stiff, slight frizz |
| Comparative Batch W | Soft, no frizz |
| Comparative Batch X | Stiff, no frizz |
| Comparative Batch Y | Soft, slight frizz |
| Comparative Batch Z | Not stiff, slightly frizzy |

The inventive compositions display reduced frizz without significantly increasing stiffness, leading to better aesthetics while achieving less frizz.

Example 6

Exemplary hair fixatives (mousses) of the present invention contain the components recited in TABLE 7 on a weight/weight basis (wt. %).

TABLE 7

| | Batch E | Batch F |
|---|---|---|
| Batch 2 ethylene/sodium acrylate copolymer (25.7%) | 1.95 | 1.95 |
| ACUDYNE 1000 acrylates/hydroxyesters acrylates Copolymer (45%) | 4.0 | 4.0 |
| ACULYN 88 Acrylates/Steareth-20 Methacrylate Crosspolymer (28%) | 2.0 | 2.0 |
| PD QUAT dihydroxypropyl trialkyl ammonium chloride | — | 0.18 |
| MACKAM 35 Cocamidopropyl Betaine | 0.5 | 0.5 |
| NEOLONE PE Phenoxyethanol/methylisothiazlinone | 0.45 | 0.45 |
| AMP-95 Amino methylpropanol | 0.42 | 0.42 |
| Water | 90.68 | 90.50 |

ACUDYNE 1000 is dispersed into water, followed by ACUDYNE 88, and the remaining components (except AMP-95) are added with overhead stirring at about 300 rpm. AMP-95 is then added gradually with mixing until a translucent solution forms.

Example 7 (Comparative)

Comparative hair fixatives (mousses) contain the components recited in TABLE 8 on a weight/weight basis (wt. %).

TABLE 8

| | Comparative Batch T | Comparative Batch U |
|---|---|---|
| AMMONYX CETAC 30 Cetrimonium Chloride (30%) | 0.3 | — |
| PD QUAT dihydroxypropyl trialkyl ammonium chloride | — | 0.18 |
| ACCUDYNE 1000 acrylates/hydroxyesters acrylates Copolymer (45%) | 4.0 | 4.0 |
| ACULYN 88 Acrylates/Steareth-20 Methacrylate Crosspolymer (28%) | 2.0 | 2.0 |
| MACKAM 35 Cocamidopropyl Betaine | 0.5 | 0.5 |
| NEOLONE PE Phenoxyethanol/methylisothiazlinone | 0.45 | 0.45 |
| AMP-95 Amino methylpropanol | 0.42 | 0.42 |
| Water | 92.33 | 92.45 |

Example 8

Compositions substantially according to the protocols of Examples 2 and 3 were prepared. Pre-washed and dried tresses of European 8-hour bleached hair (available from International Hair Importers and Products Inc.) were wetted with warm tap water, squeezed off to remove excess water, and applied 1 g of formulation test solution along the length of the hair swatches (8 inches long, weigh 5g), three (3) hair tresses per test sample.

Six experienced panelists evaluate the hair swatches for wet comb and feel. Scales are from 1 to 5, with higher number meaning better performance attributes, such as easier combability and silky feel. Hair swatches are then dried in 45C oven for 1 hr for stiffness, dry comb and feel, static and volume evaluation. Scales are from 1 to 5, with higher number meaning better performance attributes, such as high stiffness, easier combability and silky feel, no static or fly away, and more volume.

Statistical analysis was run by paired t-test: two samples assuming equal variances. The p (one tail) value smaller than 0.10, 0.05, 0.01, and 0.001, indicates one sample is significantly better than another at 90%, 95%, 99% and 99.9% confidence level respectively. P-value larger than 0.10 is considered to be statically equal.

Batch E, Comparative Batch T, and Comparative Batch U were equal for wet comb, wet feel, dry stiffness, static, and volume. At a 95% confidence level, Comparative Batch T had slightly better dry comb and dry feel over either.

Batch F and Comparative Batch T were equal for dry stiffness, dry comb, and static. Comparative Batch T had slightly better volume (90% confidence level) and dry feel (95% confidence level), however, inventive Batch F had the better wet comb (90% confidence level) and wet feel (99% confidence level). Using a DIA-STRON miniature tensile tester in a manner substantially similar to that described in Example 4, except that the work to compress the curl to 25% of its initial diameter was measured, the peak force of compression was recorded as the peak stiffness performance (gmf=grams mass force).

Batch F had a superior stiffness (812.8 gmf) compared to Comparative Batch T (627.0 gmf). This is surprisingly because conventional wisdom would predict similar stiffness, accordingly, a synergistic effect appears to be present when dihydroxypropyl trialkyl ammonium chloride is present in the inventive compositions, resulting in improved hold with good aesthetics.

It is understood that the present invention is not limited to the embodiments specifically disclosed and exemplified herein. Various modifications of the invention will be apparent to those skilled in the art. Such changes and modifications may be made without departing from the scope of the appended claims.

Moreover, each recited range includes all combinations and subcombinations of ranges, as well as specific numerals contained therein. Additionally, the disclosures of each patent, patent application, and publication cited or described in this specification are hereby incorporated by reference herein, in their entireties.

The invention claimed is:
1. A hair fixative composition, comprising
(a) from about 0.5 wt % to about 10 wt % of an aqueous dispersion comprising
(i) an ethylene acrylic acid copolymer in an amount of from about 2 wt % to about 35 wt % by weight of the aqueous dispersion, and
(ii) an ethylene/octene copolymer in an amount of from about 10 wt % to about 50 wt % by weight of the aqueous dispersion,
wherein the ethylene acrylic acid copolymer and ethylene/octene copolymer are in a polymer ratio of from about 40:60 to about 15:85, and wherein the solids content of the aqueous dispersion is in a range of from about 10 wt % to about 50 wt %, and
(b) a hair fixative resin,
wherein when the composition is applied to human hair tresses the composition provides at least 80% curl retention to tresses that are curled and exposed to 95% relative humidity at 35° C. for 2 hours.

2. The hair fixative composition of claim 1, wherein the ethylene acrylic acid copolymer is present in a range from about 4 wt % to about 20 wt % by weight of the aqueous dispersion.

3. The hair fixative composition of claim 1, wherein the ethylene/octene copolymer is present in a range from about 15 wt % to about 40 wt % by weight of the aqueous dispersion.

4. The hair fixative composition of claim 1, wherein the aqueous dispersion is present in a range from about 1 wt % to about 5 wt % by weight of the hair fixative composition.

5. The hair fixative composition of claim 1, further comprising dihydroxypropyl trialkyl ammonium chloride.

6. The hair fixative composition of claim 1, wherein the solids content of the aqueous dispersion is about 40 wt %.

7. The hair fixative composition of claim 1, wherein when the composition is applied to human hair tresses the composition provides at least 95% curl retention to tresses that are curled and exposed to 95% relative humidity at 35° C. for 2 hours.

8. The hair fixative composition of claim 1, wherein the composition is in the form of a gel or formulated for application as a spray or mousse.

9. The hair fixative composition of claim 1, wherein the composition is formulated for application as a spray or mousse.

10. A hair fixative composition, comprising
(a) from about 0.5 wt % to about 10 wt % of an aqueous dispersion comprising
(i) an ethylene acrylic acid copolymer in an amount of from about 2 wt % to about 35 wt % by weight of the aqueous dispersion, and
(ii) an ethylene/octene copolymer in an amount of from about 10 wt % to about 50 wt % by weight of the aqueous dispersion,
wherein the ethylene acrylic acid copolymer and ethylene/octene copolymer are in a polymer ratio of from about 40:60 to about 15:85, and
wherein the solids content of the aqueous dispersion is in a range of from about 10 wt % to about 50 wt %, and
(b) a hair fixative resin,
wherein the composition is in the form of a gel or formulated for application as a spray or mousse.

11. The hair fixative composition of claim 10, wherein the composition is of formulated for application as a spray or mousse.

12. A method of styling hair, comprising:
applying to dry hair the composition of claim 1.

* * * * *